United States Patent [19]

Gregson et al.

[11] 4,165,427

[45] Aug. 21, 1979

[54] 1-METHYL-9β-D-RIBOFURANOSYL-ISOGUANINE

[75] Inventors: Richard P. Gregson, Narraweena; Ronald J. Quinn, Cromer, both of Australia

[73] Assignee: Hoffmann-La Roche Inc., Nutley, N.J.

[21] Appl. No.: 930,100

[22] Filed: Aug. 1, 1978

[30] Foreign Application Priority Data

Apr. 3, 1977 [LU] Luxembourg .............................. 77910

[51] Int. Cl.² ............................................. C07H 17/00
[52] U.S. Cl. ...................................... 536/24; 424/180
[58] Field of Search ............................................. 536/24

[56] References Cited

FOREIGN PATENT DOCUMENTS

| 42-10517 | 7/1967 | Japan | 536/24 |
| 45-16713 | 10/1970 | Japan | 536/24 |

OTHER PUBLICATIONS

Kazimierczuk, Z., Chem. Abstract, vol. 80, 96289b, 1974.
Yamazaki, A., et al., Chemical Abstracts, vol. 71, 3612c (1969).
Yamazaki, A. et al., Chem. Pharm. Bull., vol. 16, 2172-2181 (1968).
Suhadolnik, R., *Nucleoside Antibiotics*, pp. 267-270, Wiley-Interscience, New York, 1970.

*Primary Examiner*—Johnnie R. Brown
*Assistant Examiner*—Blondel Hazel
*Attorney, Agent, or Firm*—Jon S. Saxe; Bernard S. Leon; Frank P. Hoffman

[57] ABSTRACT

The invention relates to a compound, 1-methyl-9β-D-ribofuranosyl-isoguanine, and to a process for the preparation thereof by isolation from natural sources. The compound has muscle relaxing, central nervous system, anti-inflammatory, anti-allergy and hypotensive activity.

2 Claims, No Drawings

1-METHYL-9β-D-RIBOFURANOSYL-ISOGUANINE

DESCRIPTION OF THE INVENTION

The invention relates to a hitherto unknown cyclic compound, namely 1-methyl 9β-D-ribofuranosyl-isoguanine, which can exist in tautomeric forms, e.g, of the formula

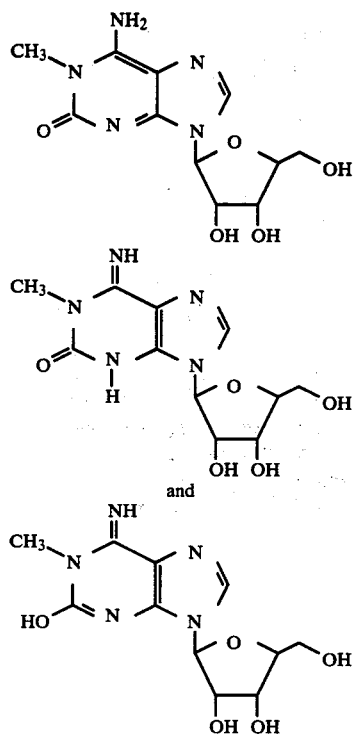

In accordance with the invention it has been found that 1-methyl-9β-D-ribofuranosyl-isoguanine is contained in low quantities in marine organisms, particularly in sponges belonging to the genus Tedania, which can be collected on the Australian sea-coasts.

Accordingly, the invention relates in one aspect to the isolation of 1-methyl-9β-D-ribofuranosyl-isoguanine from natural sources, particularly marine organisms, especially sponges of the genus Tedania.

1-Methyl-9β-D-ribofuranosyl-isoguanine in substantially pure form, i.e. free from naturally occuring by-products, thus constitutes a further feature of the present invention.

1-Methyl-9β-D-ribofuranosyl-isoguanine can be isolated from the natural source, e.g. from the sponges, in a manner known per se, for example by extraction with DMSO, water and/or an organic hydroxylic solvent, such as a lower alkanol, e.g. methanol or ethanol, an ethanol-water mixture being preferred, and subsequent chromatography, preferably ion exchange chromatography, e.g. using a cation exchange resin, such as a resin containing $SO_3H$ groups, and a mild acidic buffer, such as ammonium formate.

1-Methyl-9β-D-ribofuranosyl-isoguanine has various therapeutical activities, e.g. muscle relaxing, central nervous system, anti-inflammatory, anti-allergy and hypotensive activity. Thus, the $ED_{50}$ values for 1-methyl-9β-D-ribofuranosyl-isoguanine as a muscle relaxant in mice are 3,1 mg/kg (i.p.) and 12.0 mg/kg (p.o.). The $LD_{50}$ of 1-methyl-9β-D-ribofuranosyl-isoguanine in mice after 24 hours is 1000 mg/kg p.o.

1-Methyl-9β-D-ribofuranosyl-isoguanine is useful as a muscle relaxant and/or central nervous system active and/or anti-inflammatory and/or anti-allergy and/or hypotensive agent. It can be used in medicine in the form of pharmaceutical preparations which contain it in association with a compatible pharmaceutical carrier, namely an organic or inorganic inert carrier material suitable for enteral, preferably oral, or parenteral administration. Examples of such carrier materials are water, gelatin, lactose, starch, talc, magnesium stearate, gums, vegetable oils and petroleum jelly. The pharmaceutical preparations can be made up in a solid form, e.g. as tablets, capsules, dragees or suppositories, or in a liquid form, e.g. as solutions, emulsions or suspensions. The pharmaceutical preparations may be sterilised and/or may contain compatible adjuvants such as preservatives, stabilising agents, flavouring agents, colouring agents, emulsifying agents, salts for varying the osmotic pressure or buffering agents.

Convenient pharmaceutical dosage forms contain about 1 to 100 mg of 1-methyl-9β-D-ribofuranosyl-isoguanine. Convenient oral dosages are in the range of about 0.1 mg/kg per day to about 25 mg/kg per day. Convenient parenteral dosages are in the range of about 0.01 mg/kg per day to about 10 mg/kg per day. However, the ranges mentioned can be extended upwards or downwards depending upon individual requirements.

EXAMPLE 1

The starting material is an orange sponge of the genus Tedania which was collected on the sea-coasts of Australia. The frozen organism was lyophilized and ground. The resultant powder (300 g) was stirred with ethanol:-water (3:7 v/v, 2 l) at 4° for 24 hours, filtered, then the residue was extracted again. The combined filtrates were concentrated (35°, 7 mm) the aqueous suspension (1.2 l) was centrifuged (9000 r.p.m., 13,000×g, 0.3 h) then the supernatant was lyophilised to yield 75.7 g of the crude extract as an orange powder A.

Crude extract A (205 g) was suspended in 0.1 M ammonium formate (pH 3.5), then it was sonicated 15 min. and stirred on a boiling water bath 40 min. The suspension was cooled to 22°, its pH lowered from 4.2 to 3.5 with formic acid and then centrifuged 30 min. at 13,000 g. The supernatant was applied to a column (40×5 cm) of Bio Rad AG5OW-X8 ($NH_4^+$ form, 200–400 mesh) equilibrated in 0.1 M ammonium formate (pH 3.5), and the eluate (flow rate 150 ml pro hour) monitored in flow cells by percent transmission (254 and 280 nm). After 10 l of the starting buffer was eluted, 0.1 M ammonium formate (pH 5.3), was applied to the column. Fractions of 1.2 l (pH 3.5–4.8), 4.5 l (pH 4.8–5.0) and 5 l (pH 5.0–5.2) were collected. Only the fraction pH 4.8–5.0 was active; it was lyophilised to yield 31.6 g of a pale yellow solid B.

A solution of B (68.9 g) in 1.25 l of 0.1 M ammonium formate (pH 3.5), was centrifuged 20 min. at 13,000 g, then the supernatant was diluted to 4 l with 0.1 M ammonium formate (pH 3.5), and the pH adjusted to 3.7 with formic acid. The solution was applied to a column (41.5×5 cm) of Bio Rad AG5OW-X8 (200–400 mesh, $NH_4^+$ form) and the procedure outlined above for the treatment of the crude extract A was followed. After 5.1 l of pH 3.5 buffer was eluted, pH 5.3 buffer was applied and the active material eluted from 7.85 l to 10.85 l. Lyophilisation of the active fraction gave 10.8 g of C.

Recrystallisation of C (10.8 g) from boiling water gave 2.75 g of 1-methyl-9β-D-ribofuranosyl-isoguanine as a colourless crystalline solid, m.p. 262°–263°, $[\alpha]_{589}^{24}$ −65.4° (c=1.0, DMSO), $[\alpha]_{589}^{22}$ −54.6° (c=1.0, H$_2$O), ultraviolet: $\lambda_{max}$ 237 nm ($\epsilon$5600), 283 nm ($\epsilon$12090) pH 1.5; 250 nm ($\epsilon$8600), 294 nm ($\epsilon$11400) pH 6.3; 252 nm ($\epsilon$8400), 291 nm ($\epsilon$11200) pH 11.5.

What is claimed:

1. A compound of the formula

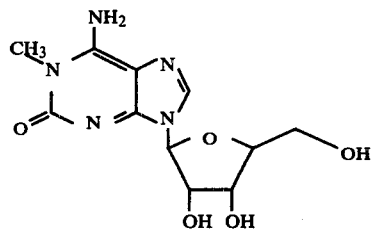

and the tautomeric forms thereof.

2. A process to produce a compound of the formula

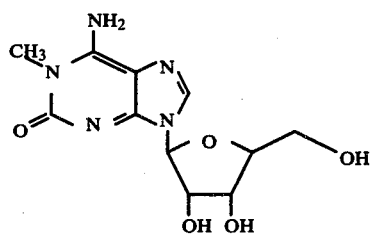

which comprises treating an orange sponge of the genus Tedania by solvent extraction with a solvent selected from the group consisting of DMSO, water or a water-/organic hydroxylic solvent mixture and thereafter purifying the extract by ion exchange chromatography.

* * * * *